(12) United States Patent
Trieu et al.

(10) Patent No.: US 7,682,393 B2
(45) Date of Patent: Mar. 23, 2010

(54) IMPLANT SYSTEM, METHOD, AND INSTRUMENT FOR AUGMENTATION OR RECONSTRUCTION OF INTERVERTEBRAL DISC

(75) Inventors: Hai H. Trieu, Cordova, TN (US); Lehmann K. Li, Milford, CT (US)

(73) Assignee: Warsaw Orthopedic, Inc.

( * ) Notice: Subject to any disclaimer, the term of this patent is extended or adjusted under 35 U.S.C. 154(b) by 858 days.

(21) Appl. No.: 10/965,589

(22) Filed: Oct. 14, 2004

(65) Prior Publication Data

US 2006/0085002 A1 Apr. 20, 2006

(51) Int. Cl.
*A61F 2/44* (2006.01)
(52) U.S. Cl. .................................... 623/17.11
(58) Field of Classification Search ... 623/17.11–17.16; 606/61, 69–71, 280–291
See application file for complete search history.

(56) References Cited

U.S. PATENT DOCUMENTS

| | | |
|---|---|---|
| 1,424,109 A | 7/1922 | McBride |
| 2,090,174 A | 8/1937 | Albright |
| 4,265,231 A | 5/1981 | Scheller, Jr. et al. |
| 4,541,423 A | 9/1985 | Barber |
| 4,751,922 A | 6/1988 | DiPietropolo |
| 4,941,466 A | 7/1990 | Romano |
| 5,002,546 A | 3/1991 | Romano |
| 5,192,326 A | 3/1993 | Bao et al. |
| 5,509,918 A | 4/1996 | Romano |
| 5,520,700 A | 5/1996 | Beyar et al. |
| 5,674,296 A * | 10/1997 | Bryan et al. ............. 623/17.16 |
| 5,690,649 A | 11/1997 | Li |
| 5,695,513 A | 12/1997 | Johnson et al. |
| 5,741,300 A | 4/1998 | Li |
| 5,843,127 A | 12/1998 | Li |
| 5,954,057 A | 9/1999 | Li |
| 6,102,934 A | 8/2000 | Li |
| 6,224,630 B1 | 5/2001 | Bao et al. |
| 6,245,107 B1 | 6/2001 | Ferree |
| 6,270,518 B1 | 8/2001 | Pedlick et al. |
| 6,287,313 B1 | 9/2001 | Sasso |
| 6,319,269 B1 | 11/2001 | Li |
| 6,328,744 B1 | 12/2001 | Harari et al. |
| 6,371,990 B1 | 4/2002 | Ferree |
| 6,402,757 B1 | 6/2002 | Moore, III et al. |
| 6,419,678 B1 | 7/2002 | Asfora |
| 6,419,704 B1 | 7/2002 | Ferree |
| 6,425,919 B1 | 7/2002 | Lambrecht |
| 6,482,235 B1 | 11/2002 | Lambrecht et al. |
| 6,562,046 B2 | 5/2003 | Sasso |
| 6,592,625 B2 | 7/2003 | Cauthen |
| 6,607,534 B2 | 8/2003 | Bonutti |
| 6,663,669 B1 * | 12/2003 | Reiley ..................... 623/21.18 |

(Continued)

FOREIGN PATENT DOCUMENTS

DE 20313512 U1 12/2003

(Continued)

*Primary Examiner*—Thomas C Barrett
*Assistant Examiner*—Michael J Araj (57) ABSTRACT

An augmentation instrument for attaching a retaining device to a vertebral endplate comprises a drive housing having a distal end portion, a drive mechanism extending through the drive housing and including a flexible shaft portion, and an attachment mechanism at the distal end portion of the drive housing. The attachment mechanism is adapted for coupling to the retaining device.

17 Claims, 6 Drawing Sheets

U.S. PATENT DOCUMENTS

| | | |
|---|---|---|
| 6,726,707 B2 | 4/2004 | Pedlick et al. |
| 6,733,531 B1 | 5/2004 | Trieu |
| 6,736,829 B1 | 5/2004 | Li et al. |
| 6,746,451 B2 | 6/2004 | Middleton et al. |
| 6,974,479 B2 * | 12/2005 | Trieu ................. 623/17.11 |
| 6,984,234 B2 * | 1/2006 | Bray ....................... 606/69 |
| 7,001,385 B2 * | 2/2006 | Bonutti ..................... 606/60 |
| 2002/0016595 A1 * | 2/2002 | Michelson ................ 606/73 |
| 2002/0123807 A1 | 9/2002 | Cauthen, III |
| 2002/0151979 A1 | 10/2002 | Lambrecht et al. |
| 2003/0004574 A1 | 1/2003 | Ferree |
| 2003/0014117 A1 | 1/2003 | Lambrecht et al. |
| 2003/0014118 A1 | 1/2003 | Lambrecht et al. |
| 2003/0040796 A1 | 2/2003 | Ferree |
| 2003/0078579 A1 | 4/2003 | Ferree |
| 2003/0093155 A1 | 5/2003 | Lambrecht et al. |
| 2003/0191536 A1 | 10/2003 | Ferree |
| 2003/0195514 A1 | 10/2003 | Trieu et al. |
| 2004/0010317 A1 | 1/2004 | Lambrecht et al. |
| 2004/0024465 A1 | 2/2004 | Lambrecht et al. |
| 2004/0030392 A1 | 2/2004 | Lambrecht et al. |
| 2004/0034429 A1 | 2/2004 | Lambrecht et al. |
| 2004/0039392 A1 | 2/2004 | Trieu |
| 2004/0078081 A1 * | 4/2004 | Ferree .................... 623/17.16 |
| 2004/0111161 A1 | 6/2004 | Trieu |
| 2005/0261774 A1 * | 11/2005 | Trieu ..................... 623/17.16 |

FOREIGN PATENT DOCUMENTS

| | | |
|---|---|---|
| EP | 0 609 084 A2 | 8/1994 |
| WO | WO 02/064044 | 8/2002 |

* cited by examiner

IMPLANT SYSTEM, METHOD, AND INSTRUMENT FOR AUGMENTATION OR RECONSTRUCTION OF INTERVERTEBRAL DISC

BACKGROUND

Intervertebral discs may be displaced or damaged due to trauma or disease resulting in disruption of the annulus fibrosis and the eventual protrusion of the nucleus pulposus into the spinal canal, a condition commonly referred to as a herniated or ruptured disc. The extruded nucleus pulposus may press on the spinal nerve, which may cause nerve damage, pain, numbness, muscle weakness and paralysis. Intervertebral discs may also deteriorate due to the normal aging process. As a disc dehydrates and hardens, the disc space height may be reduced, leading to instability of the spine, decreased mobility and pain.

Treatment to relieve the symptoms of these conditions has included partial or complete discectomy followed by fusion of the adjacent vertebrae or the installation of a mechanical motion preservation device. More recently, efforts have been directed to replacing the nucleus pulposus of the disc with an implant. However, once positioned in the disc space, implants may migrate in the disc space and/or may become expelled from the disc space through an annular defect. Tools, methods, and devices are therefore needed to repair intervertebral discs.

SUMMARY

In one embodiment, an augmentation instrument for attaching a retaining device to a vertebral endplate comprises a drive housing having a distal end portion, a drive mechanism extending through the drive housing and including a flexible shaft portion, and an attachment mechanism at the distal end portion of the drive housing. The attachment mechanism is adapted for coupling to the retaining device.

In another embodiment, a method for preventing migration of a prosthesis from an intervertebral disc space comprises providing a retaining device wherein the retaining device includes a blocking face disposed generally perpendicular to a mounting face. The method further comprises positioning the blocking face within the intervertebral disc space to prevent migration of the prosthesis and securing the mounting face to a vertebral endplate, wherein the retaining device is entirely within the intervertebral disc space.

BRIEF DESCRIPTION OF THE DRAWINGS

FIG. 3g shows an implant according to another embodiment of the present disclosure.

FIG. 3h shows an implant according to another embodiment of the present disclosure.

FIG. 3i shows an implant according to another embodiment of the present disclosure.

FIG. 4a shows a cross section view of the implant system of FIG. 3a.

DETAILED DESCRIPTION

The present invention relates generally to intervertebral disc reconstructive devices, and more particularly, to a system for retaining a prosthetic nucleus pulposus. For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
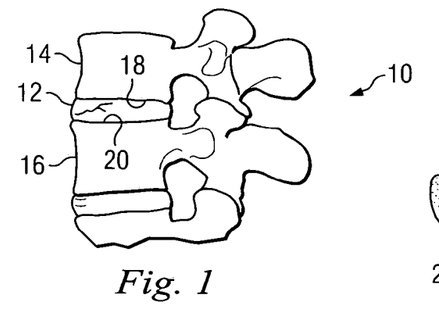
FIG. 1 is a sagittal view of vertebral column having a damaged intervertebral disc.
Figure 2:
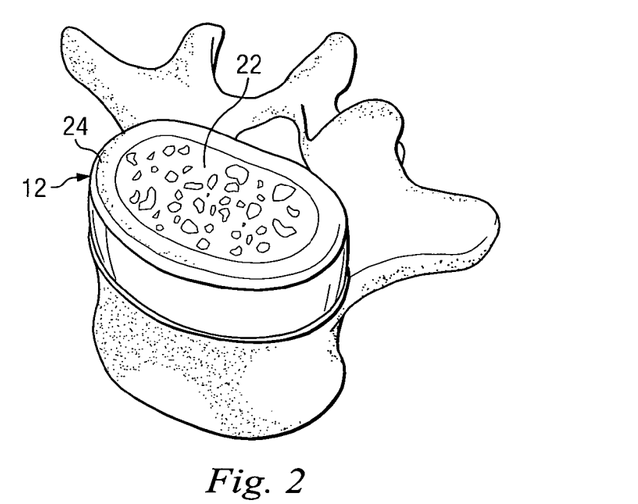
FIG. 2 shows the intervertebral disc of FIG. 1.

Referring first to FIG. 1, the reference numeral 10 refers to a vertebral column with a damaged intervertebral disc 12 extending between two intact vertebral bodies 14 and 16. Vertebral bodies 14, 16 include vertebral endplates 18, 20, respectively, interfacing the intervertebral disc 12. Referring now to FIG. 2, the damaged disc 12 may include a nucleus pulposus 22 surrounded by an annulus fibrosus 24. Repairing the damaged disc 12 may involve surgically removing all or portions of the damaged disc 12 and installing an implant system which may include nucleus pulposus replacements, partial or complete intervertebral disc replacements, and other devices for reconstructing or augmenting the intervertebral disc space. These repair procedures may be performed using an anterior, anterolateral, lateral, posterior or other approach known to one skilled in the art.

Figure 3A:
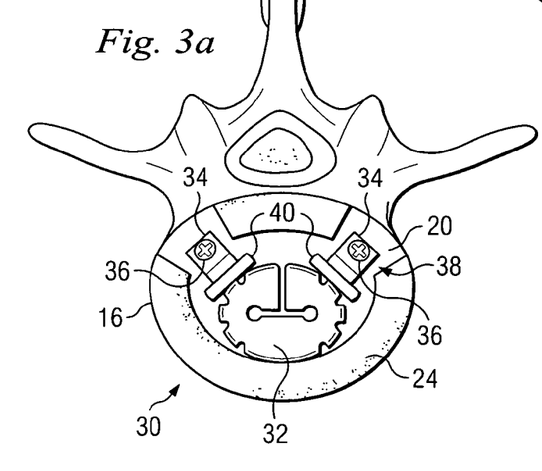
FIG. 3a shows an implant system according to one embodiment of the present disclosure.
Figure 3B:
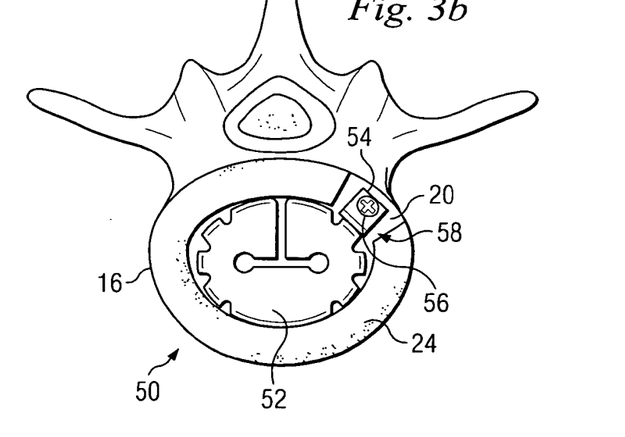
FIG. 3b shows an implant according to another embodiment of the present disclosure.
Figures 3C, 3D, 3E, 3F:
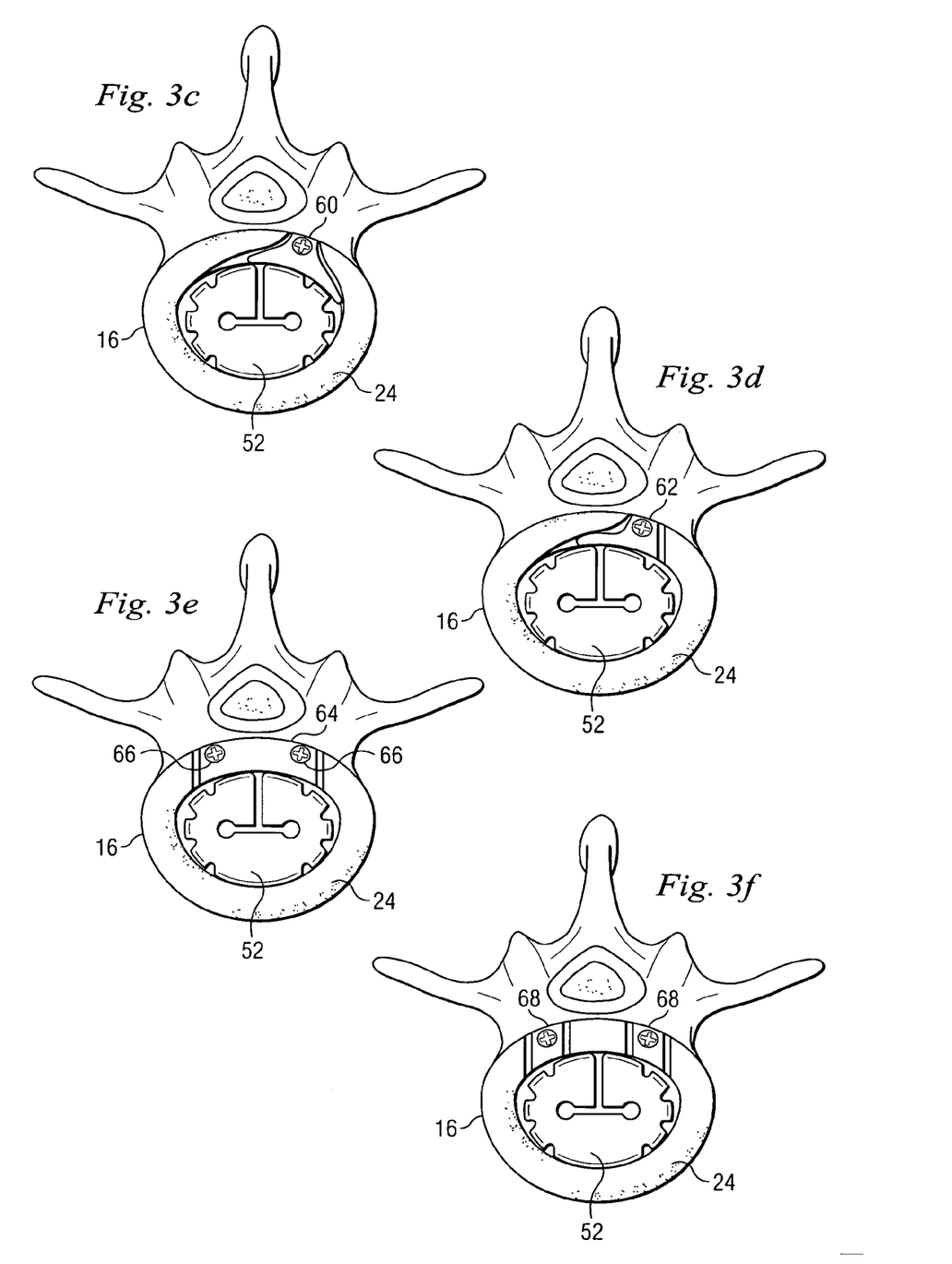
FIG. 3c shows an implant according to another embodiment of the present disclosure.
FIG. 3d shows an implant according to another embodiment of the present disclosure.
FIG. 3e shows an implant according to another embodiment of the present disclosure.
FIG. 3f shows an implant according to another embodiment of the present disclosure.
Figures 3G, 3H, 3I, 4A:
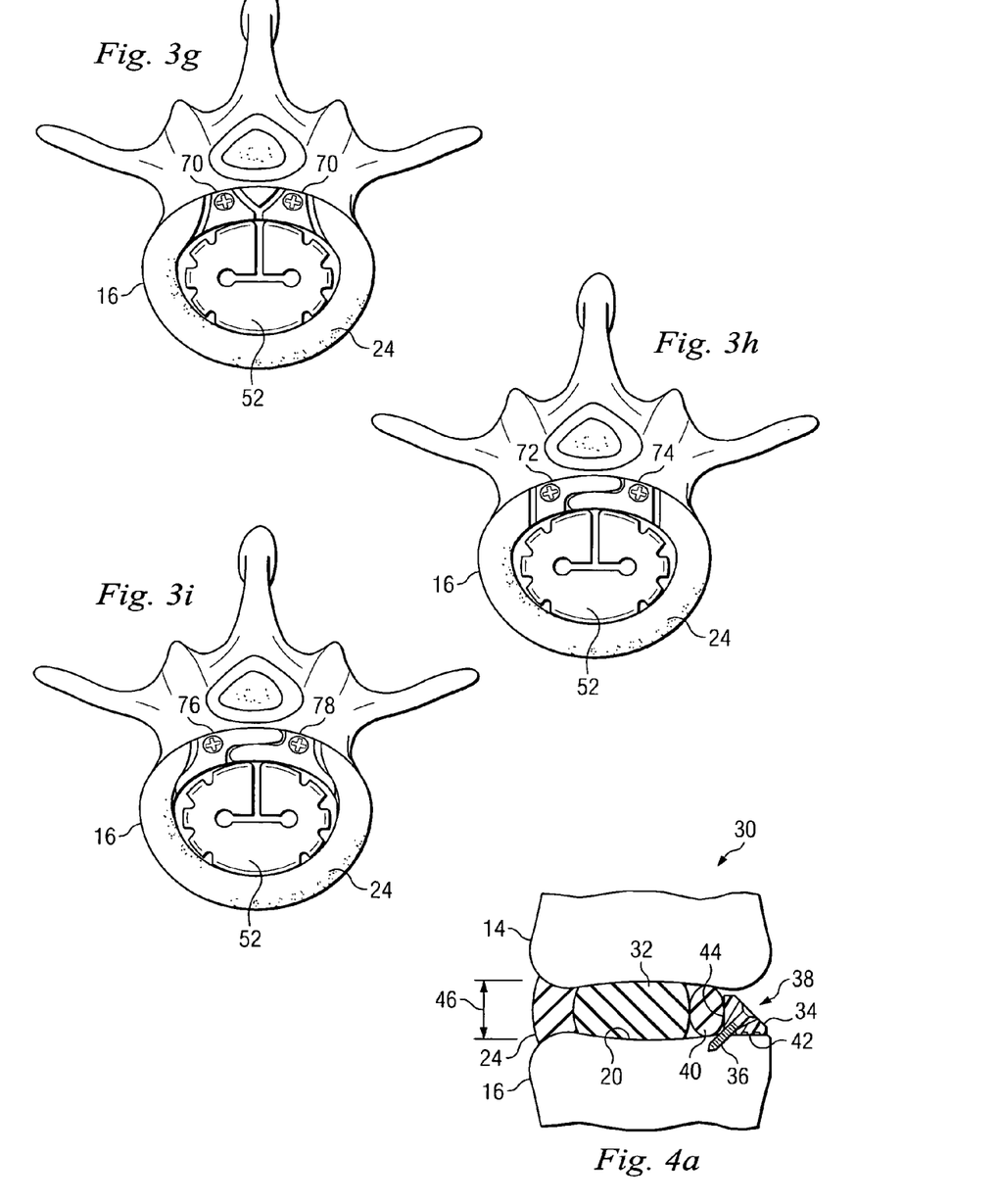

Referring now to FIGS. 3a and 4a, in one embodiment an implant system 30 may include a prosthetic nucleus 32 for replacing all or portions of the natural nucleus pulposus 22 and/or inner layers of the annulus fibrosus 24. The implant system 30 may further include one or more retaining devices such as buttress plates 34 attached to the adjacent vertebral body 16 with a fastener 36 and positioned to prevent expulsion or migration of the prosthetic nucleus 32 through an annular defect 38, such as an opening or a weak portion of the annular wall. Additionally, the implant system 30 may include one or more annular plugs 40 located between the prosthetic nucleus 32 and the buttress plates 34.

The prosthetic nucleus 32, may be of the type described in greater detail in U.S. Pat. No. 6,620,196 which is incorporated by reference herein. In one embodiment, as shown in FIG. 3a, the prosthetic nucleus 32 may generally conform to the created disc space, functioning as a flexible or an articulating spacer to prevent or slow down the collapse of the disc space while maintaining the disc's normal biomechanics. Because the annulus 24 may be difficult to surgically repair, the prosthetic nucleus 32 may have a tendency toward expulsion from the intervertebral disc space through the annulus defect 38.

In this embodiment, the prosthetic nucleus 32 may be formed of polymers such as polyurethane, copolymers of silicone and polyurethane, silicones, polyolefin rubbers, polyvinyl alcohol hydrogels, polyacrylonitrile-based hydrogels, polyacrylic-based hydrogels, or polyurethane-based hydrogels. Natural tissues may also be used including collagen-rich or connective tissues such as disc annulus, fascia lata, planar fascia, anterior or posterior cruciate ligaments, Patella tendon, Hamstring tendon, Quadriceps tendon, Achilles tendon, skin, and/or pericardium. In other embodiments the prosthetic nucleus may be a more rigid articulating body formed, for example, of polymers such as ultra-high molecular weight polyethylene (UHMWPE), polyetheretherketone, or polymethylmethacrylate; metals such as cobalt-chrome alloys, titanium, titanium alloys, stainless steel, or titanium nickel alloys; or ceramics such as alumina, zirconia, polycrystalline diamond compact, or pyrrolitic carbon.

The buttress plate 34 may provide strong resistance to prosthetic nucleus 32 expulsion even through a large annular defect 38 and may also minimize interference with the kinematics of the involved motion segment, preserving normal disc motion. The buttress plate 34 may have a relatively small size and low profile and may be generally subjected to relatively low mechanical demands. The buttress plate 34, together with the fastener 36, may fit entirely within the space between vertebral bodies 14, 16 and may be attached to at least one of the endplates 18, 20. Because the buttress plate 34 may be housed entirely within the intervertebral disc space, the damage and scarring of adjacent soft tissues may be minimized. Within the intervertebral disc space, the buttress plate 34 may have a height 39 sufficient to block expulsion of the nucleus without impacting the adjacent vertebral endplate during flexion/extension movement. For example, the height 39 may be between 2 and 12 millimeters or greater than half of the height of the intervertebral disc space.

Buttress plate 34 may be angled or wedge-shaped as shown in FIGS. 3a and 4a, or it may be another shape effective to retain the prosthetic implant member 32 in a desired location when the buttress plate 34 is secured to a vertebral body. In the embodiment shown in FIGS. 3a and 4a, for example, the buttress plate 34 includes a mounting face 42 for mounting to the endplate 20 and a retaining face 44 extending generally perpendicular to the mounting face 42 and spanning at least a portion of a cephalad-caudal distance 46 between the endplates 18, 20. The mounting face 42 may further include an aperture 48 sized to fit the fastener 36. The buttress plate 34, particularly mounting face 42, may include surface textures such as serrations, spikes, or ridges to provide better fixation to adjacent bone.

The fastener 36 may be a screw, a locking screw, a pin, a staple, or another fastening device capable of anchoring the buttress plate 34 in position. The fastener 36 may extend as far as necessary into the adjacent vertebral body to securely anchor the buttress plate 34. The fastener may be placed at an angle relative to the vertebral endplate. In some embodiments, the fastener 36 may be coated with hydroxyapetite to improve fixation to the surrounding bone.

Buttress plate 34 may be made of a rigid, biocompatible material, such as metals, ceramics, polymers, composites, tissue, or other materials. For example, suitable metals may include titanium, titanium alloy, nickel titanium alloy, stainless steel, or cobalt chrome alloy. Suitable polymers may include polyaryletherketone, polyetheretherketone, polysulfone, polyolefin, polyethylene, tyrosine-based polycarbonate, polyester, polylactide, polyglicolide, polyorthoester, polyphosphazene, polyhydroxylbutyrate, or polyhydroxylvalerate. Suitable composites may include carbon-filled composites, hydroxyl-apetite-filled composites, bioactive-glass-filled composites, and cortical-bone-chip-filled composites. Suitable tissues may include cortical bone, cancellous-cortical bone, and bone-ligament structures. In some embodiments, the bone contacting surfaces of the buttress plate 34 may be coated with hydroxyapetite to enhance fixation.

The annular plug 40 may be formed of a non-rigid material that generally conforms to the annular defect 38 and may be attached to or placed adjacent the buttress plate 34 to promote original disc mechanics. The use of the annular plug 40 in combination with the buttress plate 34 may provide an effective seal to the annular defect 38 and may reduce wear on the prosthetic nucleus 32 by preventing or limiting direct contact between the prosthetic nucleus 32 and the buttress plate 34. Further, the annular plug 40 may promote healing of the annular defect 38. The annular plug 40 may be held in place by compression, mechanical fasteners, adhesives, or other suitable means. In some embodiments, the annular plug 40 may be molded to the buttress plate 34 or attached by a dovetail joint.

The annular plug 40 may be formed of elastic or otherwise resilient materials. Examples of suitable materials may include, hydrogels, silicone, polyurethane, polyolefins such as polyisobutylene and polyisoprene, copolymers of silicone and polyurethane, neoprene, nitrile, vulcanized rubber, and/or other biocompatible elastomeric materials known in the art. Fabric or porous scaffold materials made of various synthetic or natural materials may also be suitable for forming annular plug 40. These materials may be resorbable or non-resorbable and may include, for example, polyethylene, polyester, polyvinyl alcohol, polyacrylonitrile, polyamide, polytetrafluorethylene, poly-paraphenylene terephthalamide, cellulose, silk, elastin, polylactide, polyglycolide, tyrosine-derived polycarbonate, polyanhydride, polyorthoester, polyphosphazene, polyhydroxybutyrate, and/or polyhydroxyvalerate. Natural tissues may also be suitable for forming annular plug 40. For example, autografts, allografts, or xenografts of annulus, ligament, tendon, or other connective tissues may be used.

Various alternative embodiments of the above described implant system are contemplated. The buttress plate may be available in a variety of sizes to provide surgeons with flexibility in repairing annular defects. In alternative embodiments, the angle between the mounting and retaining faces may be non-perpendicular. In alternative embodiments, the buttress plate may include additional mounting and retaining faces and may attach to both the vertebral endplates 18, 20.

In one alternative, the annular plug may be omitted, in which case, the retaining face may be smooth or polished to minimize damage to the prosthetic nucleus. Where the annular plug is omitted, the retaining face may be lined or coated to reduce wear between the buttress plate and the prosthetic nucleus. The liner or coating may be pliable to provide cushioning or relatively rigid to provide wear-resistant properties. In one example, a UHMWPE liner may be used. The thickness of the UHMWPE liner may, for example, range from 100 microns to 5 millimeters.

Related retaining systems are described in U.S. Pat. No. 6,733,531 and U.S. patent application Ser. Nos. 10/419,364; 10,123,367; and 10/399,308 which are incorporated by reference herein.

Figures 4B, 5, 6:
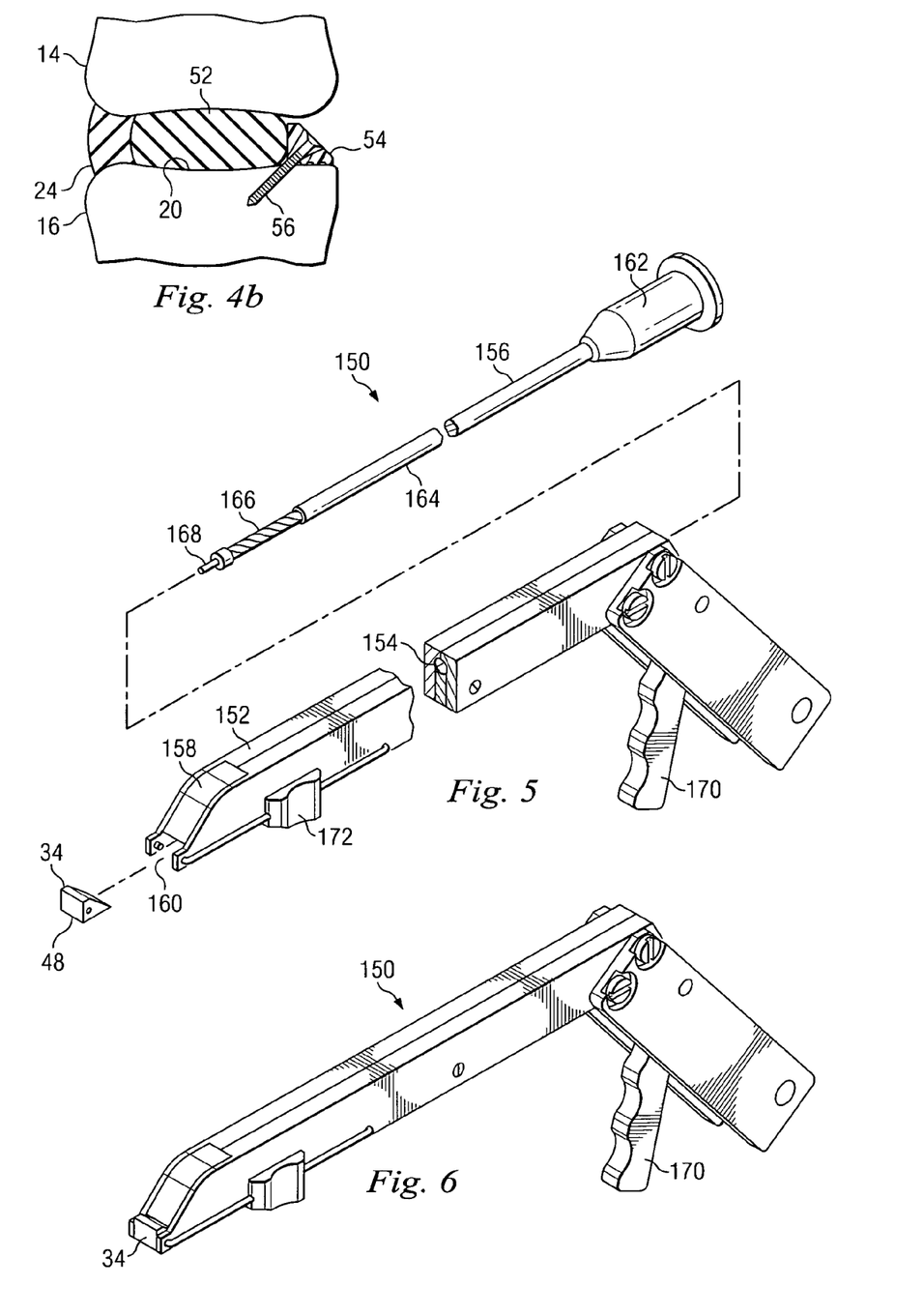
FIG. 4b shows a cross section view of the implant system of FIG. 3b.
FIG. 5 shows an augmentation instrument according to one embodiment of the present invention.
FIGS. 6-10 show a method of using the augmentation instrument.

Referring now to FIGS. 3b and 4b, in another embodiment, an implant system 50 may be substantially similar to implant system 30 and its components except for the differences described below. The implant system 50 may include a prosthetic nucleus 52 for replacing all or portions of the natural nucleus pulposus 22 and/or inner layers of the annulus fibrosus 24. The prosthetic nucleus 52 may occupy substantially all of the area vacated by the natural nucleus pulposus 22 and inner layers of the annulus fibrosus 24. The implant system 50 may further include one or more retaining devices such as buttress plates 54 attached to the adjacent vertebral body 16 with a fastener 56 and positioned to prevent expulsion or migration of the prosthetic nucleus 52 through an annular defect. Additionally, the implant system 50 may, optionally, omit an annular plug.

Referring now to FIGS. 3c, 3d, 3e, 3f, 3g, 3h, and 3i, buttress plates may be constructed in a variety of different sizes and configurations to accommodate a variety of different annular defects. The buttress plates described below may be substantially similar to buttress plate 34 except for the features described below. For example, FIG. 3c depicts a posteriorly located buttress plate 60 that extends between both sides of the adjacent annulus and the prosthetic nucleus 52. FIG. 3d depicts a buttress plate 62 that extends between one side of the adjacent annulus and the prosthetic nucleus 52. FIG. 3e depicts an elongated buttress plate 64 attached to the endplate 20 with two fasteners 66, both substantially similar to fastener 36. This elongated buttress plate 64 may be as wide as the posterior disc space and may, for example, range from 2 to 30 millimeters. FIG. 3f depicts a pair of buttress plates 68 emplaced with a bilateral approach from the posterior. FIG. 3g depicts a pair of buttress plates 70 emplaced with a bilateral approach from the posterior and tapered to extend between the remaining annulus and the prosthetic nucleus 52. FIG. 3h depicts a pair of buttress plates 72, 74 configured to overlap one another to prevent expulsion of the prosthetic nucleus 52. FIG. 3i depicts a pair of buttress plates 76, 78 configured to overlap one another to prevent expulsion of the prosthetic nucleus 52 and also configured to extend between the remaining annulus and the prosthetic nucleus 52.

Referring now to FIG. 5, an augmentation instrument 150 may be used to install or remove the buttress plate 34. The augmentation instrument 150 may include an instrument housing 152 having a bore 54 through which a driver 156 may be inserted. The instrument housing 152 may include a distal end 158 having a distal opening 160 through which the driver 156 may protrude. The distal end 158 and the corresponding portion of the bore 154 may be angled or curved.

The driver 156 may include a handle portion 162 connected to a shaft 164 having a flexible shaft portion 166 and an engagement end portion 168. The engagement end portion 168 may include, for example, a multipurpose driving tool, a drill tip, or a screwdriver tip. The engagement end portion 168 may be integral with the shaft 164 or may be separable from the shaft 164. A series of drivers may be used to complete an entire procedure.

With the driver 156 inserted through the bore 154, the engagement end portion 168 may protrude from the distal opening 160. The flexible shaft portion 166 may bend as it passes through the angled distal portion 158. The augmentation instrument 150 may further include an actuator system 170 which may be selectively activated to cause further bending of the flexible shaft portion 166. An attachment mechanism 172 may be used to selectively couple and decouple a buttress plate 34 to and from the augmentation instrument 150. The attachment mechanism 172 may include mechanical, magnetic, or other coupling means known in the art. In one embodiment, an attachment mechanism may include wire hooks attachable to and releasable from small holes on either side of the buttress plate 34.

A method for augmenting or reconstructing an intervertebral disc by installing a device, such as a buttress plate 34, to a vertebral endplate 20 will be described. Using an anterior, anterolateral, lateral, posterior or a combination approach, a discectomy and/or nucleotomy may be performed. The procedure may result in the annular defect 38. Although shown in a posterior location, it is understood that the annular defect may be located anteriorly or elsewhere along the intervertebral disc space, and thus the buttress plate 34 may be located in posterior, anterior, lateral, or other locations of the annular defect. The prosthetic nucleus 32 may be inserted through the annular defect 38 and seated between vertebral bodies 14, 16. In some embodiments, the annular plug 40 may be inserted at the site of the annular defect 38 to promote sealing and to cushion the interface between the prosthetic nucleus 32 and the buttress plate 34. In some embodiments, cartilaginous layers of the vertebral endplate 20 at the location of the buttress plate 34 may be removed to promote better bony contact and bonding between the endplate 20 and the buttress plate 34.

Figure 7:
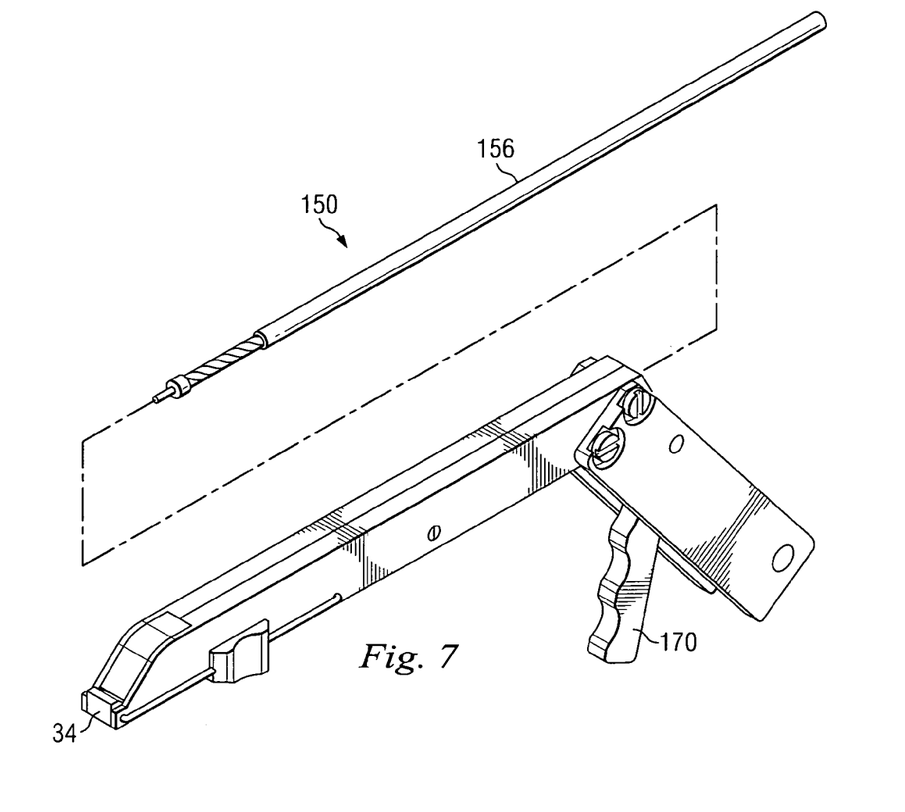

Referring now to FIGS. 6-10, the buttress plate 34 may be installed to promote healing of the annular defect 38 while retaining the prosthetic nucleus 32 in a desired position between vertebral bodies 14, 16. As shown in FIG. 6, the buttress plate 34 may be loaded to the distal portion 158 of augmentation instrument 150 and held in place with the attachment mechanism 172. As shown in FIG. 7, a driver 156, which may be a drill 180 having a drill tip 182 and a flexible shaft portion 184, may be inserted through the bore 154 of the augmentation instrument 150. The drill tip 182 may protrude from the distal opening 160.

Figure 8:
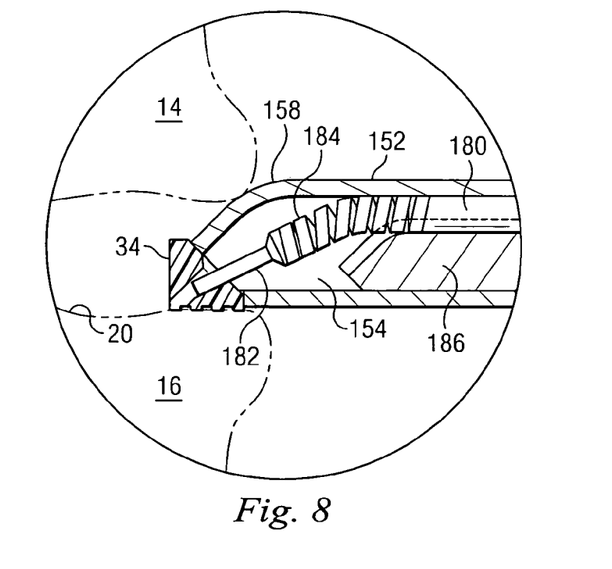

As shown in FIG. 8, the angled shape of the distal portion 158 in combination with the actuator system 170, which in this embodiment includes a slidable support 186, may cause the drill tip 182 to bend at the flexible shaft portion 184. Specifically, the slidable support 186 may be advanced by depressing the trigger 170, placing a force on the flexible shaft portion 184 and causing it to bend. This bending may allow the drill tip 182 to access confined spaces, such as the intervertebral disc space between vertebral bodies 14, 16, with minimal displacement and damage to surrounding tissues. The drill tip 182 may penetrate the pre-existing aperture 48 in the buttress plate 34 and may be activated to drill an angled hole 188 (see FIG. 9) into the vertebral endplate 20. In alternative embodiments, where an aperture is not located in the mounting face of the buttress plate, the drill tip may drill through the mounting face of the buttress plate and into the vertebral endplate 20.

Figure 9:
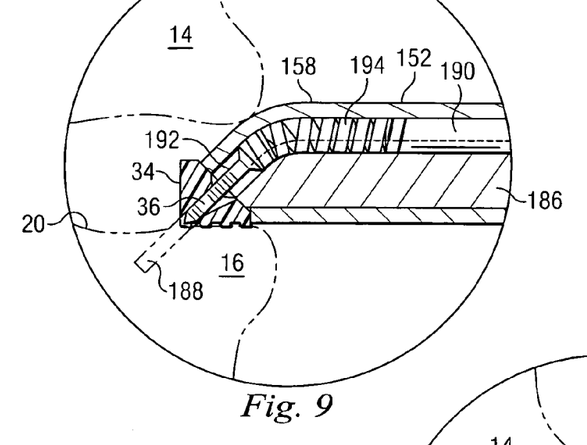
Figure 10:
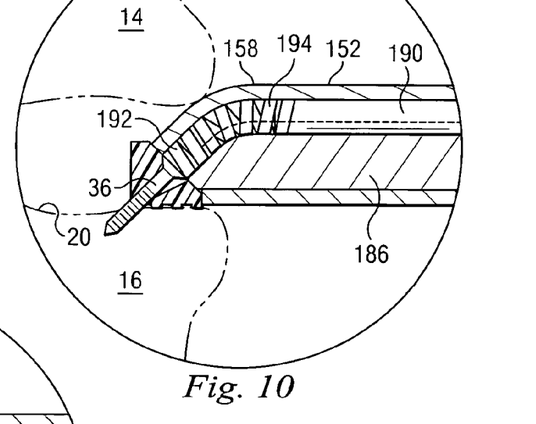

Referring now to FIGS. 9-10, after the hole 188 is created, the drill 180 may be removed and replaced with a driver 156, which may be a screwdriver 190 having a driving tip 192 and a flexible shaft portion 194. The fastener 36, which may be a screw, may be coupled to the driving tip 192. The fastener 36 and the screwdriver 190 may then be inserted through the bore 154 of the augmentation instrument 150 such that the fastener 36 protrudes through the distal opening 160. The screwdriver 190 may be activated to drive the fastener 36 into the angled hole 188. As the screw 36 engages the angled hole 188, the buttress plate 34 may be come secured to the vertebral endplate 20. The buttress plate 34 may be positioned such that the retaining face 44 blocks the annular defect 38. The secured buttress plate 34, including mounting face 42 and retaining face 44, may be positioned entirely between the vertebral endplates 18, 20 with retaining face 44 projecting in a generally cephalad-caudal direction. Securing the buttress plate 34 within the intervertebral space may reduce soft tissue damage and interference associated with external fastening mechanisms. With the buttress plate 34 secured, the attachment mechanism 172 may be released, causing the buttress plate 34 to become decoupled from the augmentation instrument 150. If revision becomes necessary, the buttress plate 34 may also be removed using the augmentation instrument 150.

Another type of fastener such and a nail or staple may be used as an alternative to the screw. In an alternative embodiment, the drilling may take place without the buttress plate 34 attached to the augmentation instrument 150. In this embodiment, the buttress plate 34 can be attached after the hole 184 is drilled and as the fastener 36 is introduced.

It is understood that the augmentation instrument and the method of use described above may also be used to install buttress plates of various sizes, shapes, and configurations, including those described in FIGS. 3b, 3c, 3d, 3e, 3f, 3g, 3h, 3i, and 3j. Although augmentation instrument 150 may be well suited for installing the buttress plate 34, any of a variety of other instruments with which surgeons are familiar and comfortable may also be used to secure the buttress plate 34 to the vertebral endplate 20.

Figure 11:
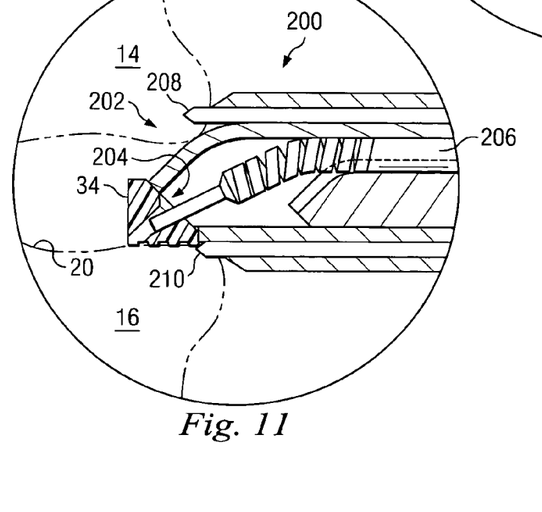
FIG. 11 shows an augmentation instrument according to another embodiment of the present invention and a method of using this augmentation instrument.

Referring now to FIG. 11, in an alternative embodiment, an augmentation instrument 200 may be substantially similar to the augmentation instrument 150 except for the features described below. The augmentation instrument 200 may include an distal end 202 having a distal opening 204 through which a driver 206 may protrude. The augmentation instrument 200 may further include stabilizers 208, 210 protruding from the distal end 202 to engage the vertebral bodies 14, 16, respectively.

During a procedure to install the buttress plate 34, the distal end 202 of the augmentation instrument 200 may be positioned between vertebral bodies 14 and 16, and the stabilizer 208 may be advanced to engage the vertebral body 14. The stabilizer 208 may be selectively extendable. For example, during the initial positioning of the augmentation instrument 200, the stabilizer 208 may be in a retracted position within the instrument. After the instrument 200 is located in a desired position, the stabilizer 208 may be selectively extended and locked to hold the instrument 200 in its desired position.

The deployed stabilizer 208 may prevent shifting of the distal end 202 during subsequent drilling and buttress plate installation procedures. The stabilizer 208 may also maintain precise placement of the distal end 202 while drivers are interchanged. In this embodiment, the stabilizer 208 may be a sliding pin, but other stabilizing structures such as screws, stables, or clamps may be acceptable alternatives. The stabilizer 208 may extend into the vertebral body 14 along an axis defined by the instrument 200 as shown in FIG. 11, but in alternative embodiments the stabilizer may be deployed at an angle. It is understood that stabilizer 210 may be activated in a same or similar manner as stabilizer 208 and thus will not be separately described in detail. Stabilizer 210 may also be deployed together with or independently from stabilizer 208.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A system for maintaining a nucleus prosthesis within an annulus having a defect, the system comprising:
a first blocking plate for preventing migration of the nucleus prosthesis through the defect in the annulus, the first blocking plate sized to be positioned substantially within an intervertebral disc space defined by a pair of adjacent vertebral endplates, the first blocking plate having a height less than a distance between the adjacent vertebral endplates but greater than half of the distance between the adjacent vertebral endplates such that the first blocking plate prevents migration of the nucleus prosthesis through the defect in the annulus without limiting the natural flexion and extension of the adjacent vertebral endplates, the first blocking plate comprising:
a substantially planar retaining face,
a substantially planar mounting face extending substantially perpendicular to the retaining face for engagement with a single one of the adjacent vertebral endplates, and
an aperture extending through the first blocking plate and through a portion of the mounting face,
wherein the first blocking plate comprises a rigid, non-resorbable biocompatible material;
a fastener sized and shaped for extending through the aperture in the first blocking plate and into the single one of the adjacent vertebral endplates to securely attach the first blocking plate to the single one of the adjacent vertebral endplates; and
an annular plug sized and shaped for positioning between the nucleus prosthesis and the first blocking plate at least partially within the defect in the annulus.

2. The system of claim 1, wherein the annular plug is attached to the first blocking plate.

3. The system of claim 2, wherein the annular plug is molded to the first blocking plate.

4. The system of claim 2, wherein the annular plug is attached to the first blocking plate with a dovetail joint.

5. The system of claim 1, wherein the annular plug is formed of a resilient material.

6. The system of claim 5, wherein the resilient material is non-resorbable.

7. The system of claim 1, wherein the annular plug is formed from a natural tissue.

8. The system of claim 7, wherein the pliable material comprises a liner having a thickness between about 100 microns and about 5 millimeters.

9. The system of claim 1, wherein the mounting face comprises roughened surface texture.

10. The system of claim 9, wherein the retaining face comprises a smooth surface texture.

11. The assembly of claim 9, wherein the mounting face is at least partially coated with hydroxyapetite.

12. The assembly of claim 1, wherein the retaining face comprises a pliable material.

13. The system of claim 12, wherein the pliable material comprises ultra high molecular weight polyethylene.

14. The system of claim 1, wherein the rigid, non-resorbable biocompatible material comprises a ceramic.

15. The system of claim 1, wherein the rigid, non-resorbable biocompatible material comprises a polymer.

16. The system of claim 1, wherein the first blocking plate has a wedge shape.

17. The system of claim 1, wherein the rigid non-resorbable biocompatible material comprises a metal.

* * * * *